US005565318A

United States Patent [19]
Walker et al.

[11] Patent Number: 5,565,318
[45] Date of Patent: Oct. 15, 1996

[54] ROOM TEMPERATURE STABLE REAGENT SEMI-SPHERES

[75] Inventors: David W. Walker, Milwaukee; Robert A. DiFrancesco, Hales Corners; Jean A. Heaster, Brookfield; James F. Jolly; Chris R. Lively, both of Glendale; Suzanne B. Treml, Milwaukee, all of Wis.

[73] Assignee: Pharmacia Biotech, Inc., Milwaukee, Wis.

[21] Appl. No.: 300,015

[22] Filed: Sep. 2, 1994

[51] Int. Cl.$^6$ .............................. C12Q 1/00; C12Q 1/37; G01N 33/53

[52] U.S. Cl. .................... 435/4; 435/24; 435/23; 435/18; 435/15; 435/16; 435/7.91; 435/68.1; 435/183; 435/174; 435/178; 435/179; 435/188; 435/810; 435/975; 436/17

[58] Field of Search .................... 435/4, 24, 23, 435/18, 15, 16, 7.91, 84, 85, 68.1, 183, 174, 178, 179, 188, 810, 975; 514/54, 53, 57, 59; 436/17

[56] References Cited

U.S. PATENT DOCUMENTS

| | | | |
|---|---|---|---|
| 3,300,474 | 1/1967 | Flodin et al. | 260/209 |
| 3,456,050 | 7/1969 | Rieckmann et al. | 424/35 |
| 3,721,725 | 3/1973 | Briggs et al. | 264/6 |
| 3,932,943 | 1/1976 | Briggs et al. | 34/5 |
| 4,134,943 | 1/1979 | Knitsch | 264/28 |
| 4,372,942 | 2/1983 | Cimiluca | 424/16 |
| 4,423,086 | 12/1983 | Devos et al. | 427/3 |
| 4,559,298 | 12/1985 | Fahy | 435/1 |
| 4,655,047 | 4/1987 | Temple et al. | 62/64 |
| 4,712,310 | 12/1987 | Roy | 34/5 |
| 4,753,790 | 6/1988 | Silva et al. | 424/440 |
| 4,762,857 | 8/1988 | Bollin, Jr. et al. | 514/777 |
| 4,780,285 | 10/1988 | Kuypers et al. | 422/102 |
| 4,806,343 | 2/1989 | Carpenter et al. | 424/450 |
| 4,820,627 | 4/1989 | McGeehan | 435/4 |
| 4,848,094 | 7/1989 | Davis et al. | 62/64 |
| 4,863,856 | 9/1989 | Dean, Jr. et al. | 435/68 |
| 4,891,319 | 1/1990 | Roser | 435/188 |
| 4,897,353 | 1/1990 | Carpenter et al. | 435/188 |
| 4,898,781 | 2/1990 | Onouchi et al. | 428/402.22 |
| 4,997,654 | 3/1991 | Corsello et al. | 424/440 |
| 5,098,893 | 3/1992 | Franks et al. | 514/54 |
| 5,200,399 | 4/1993 | Wettlaufer et al. | 514/23 |
| 5,240,843 | 8/1993 | Gibson et al. | 435/188 |
| 5,250,429 | 10/1993 | Jolly et al. | 435/18 |
| 5,288,502 | 2/1994 | McGinity et al. | 424/484 |

FOREIGN PATENT DOCUMENTS

| | | |
|---|---|---|
| 0252750 | 1/1988 | European Pat. Off. .......... C12Q 1/28 |
| 0383569 | 8/1990 | European Pat. Off. . |
| 60-129102 | 7/1985 | Japan . |
| WO86/00336 | 1/1986 | WIPO .............. C12N 9/92 |
| WO93/04195 | 3/1993 | WIPO .............. C12Q 1/32 |

OTHER PUBLICATIONS

Ramanujam et al, "Biotechniques", vol. 14, No. 3 (1993) pp. 470–474.

A. Kassem, et al., "Preparation of Non–pareil Seeds . . . ", 40 *Pharm. Ind.* 396–399 (1978).

M. Brophy, et al., "Influence of coating and core modifications . . . ", 33 *J. Pharm. Pharmacol.* 495–499 (1981).

I. Ghebre–Sellassie, et al., " . . . High Speed Pelletization . . . ", 11 *Drug Devel. & Indus. Pharm.* 1523–1541 (1985).

G. Orndorff, et al., " . . . Preservation of *E. coli*", 10 *Cryobiology* 475–487 (1973).

A. MacKenzie, "Collapse during freeze drying . . . ", in *Freeze Drying and Advanced Food Technology*, S. Goldblith, et al. (Eds.), Academic Press, London, pp. 277–307 (1975).

J. Carpenter, et al., "Stabilization of Phosphofructokinase . . . " 24 *Cryobiology* 455–464 (1987).

F. Franks, ". . . Stabilization of Biologicals", 12 *Bio/Technology* 253–256 (1994).

*Primary Examiner*—John Kight
*Assistant Examiner*—Louise N. Leary
*Attorney, Agent, or Firm*—Quarles & Brady

[57] ABSTRACT

A reagent semi-sphere is disclosed comprising at least one biological reagent and a glass forming filler material in a concentration sufficient to facilitate formation of a glassy, porous composition, wherein the reagent semi-sphere is room temperature stable, water soluble, and has a $T_g$ above room temperature. A method is provided for making the reagent semi-sphere comprising providing an aqueous solution of a buffered biological reagent; mixing a glass forming filler material with the buffered reagent solution to form an emulsion wherein the concentration of the filler material is sufficient to facilitate formation of a glassy, porous composition having a predetermined semi-spherical shape; dispensing the emulsion in the form of substantially uniform droplets; collecting the droplets on an inert medium to form semi-spheres; and vacuum drying the droplets, under conditions suitable for maintaining the predetermined semi-spherical shape, to form the reagent semi-sphere; wherein the reagent semi-sphere is room temperature stable, water soluble, and has a $T_g$ above room temperature.

24 Claims, No Drawings

ROOM TEMPERATURE STABLE REAGENT SEMI-SPHERES

BACKGROUND OF THE INVENTION

1. Field of the Invention

This invention relates to the long-term storage of biological materials and reagents. In particular, it relates to compositions for glassy and porous room temperature stable biological reagent semi-spheres and methods for making the same.

2. Background of the Art

Few biologically active materials are sufficiently stable so that they can be isolated, purified, and then stored in solution at room temperature. Typically, biological reagents are stored in a glycerol solution which is maintained at temperatures of 4° C., −20° C., or −70° C. They may be stored in bulk and then combined with other reagents before use.

Biological reagents are sometimes also provided in dried form to increase their storage stability. Furthermore, in preparing reagents for convenient and efficient testing of biological samples, it is frequently important to obtain dry chemical blends in uniform, discreet amounts. These reagents must be efficiently and economically prepared in small, precisely measured quantities. Current technology for producing dry biological reagent compositions involves procedures such as dry-blending, spray-drying, freeze-drying, fluidized bed drying, and/or cryogenic freezing. All these procedures, however, have limitations and drawbacks.

In dry-blending technology, it is often difficult to obtain homogeneous blends of chemicals due to their different densities. Furthermore, homogeneity is especially difficult to achieve when very small amounts of ingredients are mixed with large amounts of others. Even if homogeneity is achieved, it is most difficult to reproducibly dispense small amounts of the blended biological chemicals.

Spray-drying technology provides more homogeneous blends of chemicals because the reagents are first dissolved in solution. See U.S. Pat. No. 4,712,310. For an example of the use of spray-drying along with fluidized bed technology see A. Kassem, et al., 40 *Pharm. Ind.* 396–399 (1978) and M. Brophy, et al., 33 *J. Pharm. Pharmacol.* 495–499 (1981). With spray-drying, however, it is difficult to dispense precise amounts of blended chemicals. To overcome this drawback, the resulting particles are usually reprocessed by agglomeration to obtain uniform particle sizes such as tablets. However, the agglomerated particles are generally less soluble than the original spray-dried particles or powders. Also, these procedures sometimes use fluorocarbon cryogenic solutions which can be hazardous to the environment. The disclosure of the above articles and patents, and of all other articles and patents recited herein, are incorporated by reference as if fully set forth herein.

Fluid bed technology relies upon spraying a liquid reagent blend onto a particle and drying the composition to obtain a particle coated with blended reagents. For examples of this technology, ..See, for example, U.S. Pat. No. 4,820,627 and I. Ghebre-Sellassie, et al., 11 *Drug Devel. and Indus. Pharm.* 1523–1541 (1985). However, using fluid bed technology, it is difficult to obtain uniformly sized particles and to produce a uniform coating.

Another method for stabilizing biologicals is freeze-drying. For examples of various applications of freeze-drying technology see, for example, G. Orndorff, et al., 10 *Cryobiology* 475–487 (1973); A. MacKenzi, in *Freeze-drying and Advanced Food Technology*, S. Goldblith, et al. (Eds.), Academic Press, London (1975); U.S. Pat. No. 3,721,725; U.S. Pat. No. 4,134,943; U.S. Pat. No. 4,762,857; U.S. Pat. No. 4,806,343; U.S. Pat. No. 4,897,353; and Japanese patent Application No. 0129102. One drawback to the freeze-drying is the use of fluorocarbon refrigerants which may be dangerous to the environment. Furthermore, freeze-drying is costly in capital and energy, and also suffers from technical disadvantages because of its irreproducibility. Moreover, this process can only be applied to freeze stable biologicals.

Another method of stabilizing biologicals is by air-drying biological reagent compositions. For examples of air-drying of biological compositions using disaccharides as stabilizers see J. Carpenter, et al., 24 *Cryobiology* 455–464 (1987) and U.S. Pat. No. 4,891,319. Some problems with air drying processes are that the dried product is not in readily dispensable form. Also, the biological reagents must be stable at or above the temperature of the drying process.

One specialized process using freeze-drying technology is the formation of droplets or spheres which are contacted with a cryogenic liquid and then freeze-dried. For examples see U.S. Pat. No. 3,932,943; U.S. Pat. No. 4,780,285; U.S. Pat. No. 4,848,094; U.S. Pat. No. 4,863,856; and PCT Application WO93/04195. One drawback of this technology is that the reagent spheres are fragile and tend to disintegrate.

One type of carrier or filler which has been used to stabilize biological reagents are glass forming filler materials. The biological reagent solutions are incorporated into the glass forming filler materials (which are water soluble or a water-swellable substance). They are then dried to produce a glassy composition which immobilizes and stabilizes the biological reagent. For examples of glass forming filler materials for stabilizing biological reagents see, for example, F. Franks, 12 *Bio-Technology* 253 (1994); U.S. Pat. No. 5,098,893; U.S. Pat. No. 5,200,399; and U.S. Pat. No. 5,240,843.

Carbohydrates such as glucose, sucrose, maltose or maltotriose are an important group of glass forming substances. Other polyhydroxy compounds can be used such carbohydrate derivatives like sorbitol and chemically modified carbohydrates. Another important class of glass forming substances are synthetic polymers such as polyvinyl pyrrolidone, polyacrylamide, or polyethyleneimine.

Further examples of glass forming substances include sugar copolymers such as those sold by Pharmacia under the registered trademark FICOLL. FICOLL polymer is disclosed in U.S. Pat. No. 3,300,474 which describes the materials as having molecular weights of 5,000 to 1,000,000 and as containing sucrose residues linked through ether bridges to bifunctional groups. Such groups may be an alkylene of 2, 3 or more carbon atoms but not normally more than 10 carbon atoms. The bifunctional groups serve to connect sugar residues together. These polymers may, for example, be made by reaction of sugar with a halohydrin or bis-epoxy compound. A glass forming filler material is typically defined as an undercooled liquid with a very high viscosity, that is to say at least $10^{13}$ Paxs, probably $10^{14}$ Paxs or more.

One drawback of the aforementioned references is that normally the stabilized and glassified biological materials are ground into powders, compounded into tablets, or maintained in a thin glassy film in a container like a microcentrifuge tube. This type of packaging is generally inconvenient because dosages of a powdered material are difficult to measure, compounded tablets are slow to dissolve, and excessive sample is needed to dissolve a thin glassy film disposed in a microcentrifuge tube.

Numerous methods to make and use compositions of glassy immobilized biological materials have been tried. One system mentioned above is utilizing a thin glassy film dried and disposed in a container suitable to the final user, such as a microcentrifuge tube. However, attempts have been made to reduce the associated packaging cost by converting the glassy format to a tablet, pellet, or sphere which could be packaged in bulk containers ready for individual use. Various techniques have been tried such as a tablet press, centrifugal granulator, and fluid bed coating and vacuum drying droplets on a flat surface. Each process resulted in limited success.

The tablet press makes easily handled pills but the pills dissolve slowly. The use of tabletting excipients designed to increase dissolution speed interfere with enzyme activity. The centrifugal granulator makes spheres but the size distribution was too large to make individual dispensing practical and all enzyme activity was lost during the drying step. Fluid bed coating made spheres with good size distribution, and activity, but poor solubility. Vacuum drying droplets with a standard low viscosity solution, such as 8%–20% solids, produced flat fragile disks which dissolved slowly.

Glassy substances are also used as hard coatings for candies and pharmaceuticals. Examples of these are found in U.S. Pat. No. 3,456,050; U.S. Pat. No. 4,372,942; U.S. Pat. No. 4,423,086; U.S. Pat. No. 4,559,298; U.S. Pat. No. 4,753,790; U.S. Pat. No. 4,898,781; U.S. Pat. No. 4,997,654; PCT Publication No. W086/00336; and European Patent Application No. 0 252 750.

Accordingly, there is a need for a glassy format biological reagent which possesses excellent water solubility and dissolution rate, possesses a porous structure to assist with dissolution, avoids the typically fragile nature of the reagent spheres disclosed in PCT Publication No. W093/04195 (supra), can be made by a method which allows manipulation of droplet size characteristics, and which can be dispensed from a holder such as that disclosed in U.S. Pat. No. 4,780,285.

SUMMARY OF THE INVENTION

We have discovered an emulsion of glass forming filler material, biological reagent, and water which provides a viscosity such that controlled droplets can be dispensed on an inert surface and vacuum dried so as to form a new semi-spherical biological reagent having the above-mentioned advantages.

In a first aspect of the invention, the invention provides a biological reagent semi-sphere comprising at least one biological reagent and a glass forming filler material in a concentration sufficient to facilitate formation of a glassy, porous composition. The reagent semi-sphere is room temperature stable, water soluble, and has a $T_g$ sufficient for storage at a temperature of at least 22° C.

The biological reagent semi-sphere is preferably capable of completely dissolving in less than about 100 µl of aqueous solution in about 2 minutes. The reagent semi-sphere preferably has a moisture content of less than 10%. The reagent semi-sphere may have a diameter of about 2 mm to about 6 mm. Preferably, the reagent semi-sphere has a diameter of about 2.5 mm.

The reagent semi-sphere may have at least one reagent which is unstable when alone in an aqueous solution at room temperature. The reagent semi-sphere may also comprise a plurality of reagents which may or may not react with each other when in aqueous solution at room temperature.

The biological reagent used in the semi-sphere is selected from at least one of the group consisting of DNA/RNA modifying enzymes, restriction enzymes, nucleotides, oligonucleotides, proteins, enzymes, DNA, and nucleic acids.

The glass forming filler material is selected from at least one of the group consisting of carbohydrates (such as mono-, di-, or tri-saccharides), carbohydrate derivatives which are polyhydroxy compounds, collagens, sugar polymers containing sugar residues linked through ether bridges to bifunctional groups other than carbohydrate, and proteins. The glass forming filler material is preferably a sugar polymer containing sugar residues linked through other bridges to bifunctional groups other than carbohydrates. If a sugar polymer is used it is preferably FICOLL polymer. The glass forming filler material may also comprise proteins (such as collagen, bovine serum albumin (BSA), or gelatin), with the proteins preferably being BSA.

In another version of the invention a reagent kit is provided comprising at least one reagent semi-sphere according to the first version of the invention, a tube containing the at least one reagent semi-sphere, a sealed foil pouch containing the tube and a desiccant, and, optionally, a dispenser device adapted for individually dispensing at least one reagent semi-sphere.

A further version of the invention provides a method of making a reagent semi-sphere comprising the steps of: providing an aqueous solution of a buffered biological reagent; mixing a glass forming filler material with the buffered biological reagent solution to form a mixture wherein the concentration of the filler material is sufficient to facilitate formation of a glassy, porous composition having a predetermined semi-spherical shape; dispensing the mixture in the form of substantially uniform droplets; collecting the droplets on an inert medium to form semi-spheres; and drying the droplets, under conditions suitable for maintaining the predetermined semi-spherical shape, to form the reagent semi-sphere; wherein the reagent semi-sphere is room temperature stable, water soluble, and has a $T_g$ above room temperature. The mixture is preferably an emulsion or a semi-emulsion.

Preferably, the emulsion contains about 52% to about 62% solids. A semi-emulsion preferably contains about 10% to about 50% solids. Preferably, the first portion of drying is at about 300 Torr and at about 10° C. Preferably, the first portion of drying is about one hour. It is preferred that the drying is continued so that the reagent semi-sphere contains less than about 10% moisture. The inert medium may be a solid inert surface, a cryogenic liquid, or a cryogenically cooled inert solid surface. One aspect of the solid inert surface may include concave dimples.

A final aspect of the invention provides a reagent semi-sphere made according to the above method.

It is therefore an objective and advantage of the present invention to provide a biological reagent semi-sphere and methods of making the same. Other objects and advantages of the present invention are:

(a) providing a emulsion of biological reagent(s), glass forming filler material, and water wherein the shape of droplets formed on an inert surface can be controlled by changing the percent solids of the emulsion;

(b) wherein the shape of the droplet can be varied by changing the surface composition or shape of the drying surface;

(c) wherein the shape of the droplets can be controlled by manipulating the vacuum level during drying;

(d) wherein the drying rate can be used to preserve the shape and activity of the reagent semi-sphere;

(e) providing a reagent semi-sphere which is resistant to degradation and mechanical shock;

(f) providing a reagent semi-sphere having a porous structure which assists in the dissolution rate of the reagent sphere;

(g) providing reagent semi-spheres which can be dispensed individually from an appropriately adapted dispenser device; and (h) providing stable storage of a biological reagent that would otherwise be unstable when alone in an aqueous solution at room temperature and providing stable storage of a plurality of biological reagents that would otherwise react with each other when in an aqueous solution at room temperature.

These and still other objects and advantages of the invention will be apparent from the description below. However, this description is only of the preferred embodiments. The claims, therefore, should be looked to in order to assess the whole scope of the invention.

DETAILED DESCRIPTION OF THE INVENTION

The semi-sphere of the present invention may be any generally spherical form but less than a whole sphere. Thus, the present invention is not intended to be limited to half spheres. Room temperature is defined as being about 22° C.

Iterative Process

The formulation of a high viscosity mixture of biological reagent, glass forming filler material, and water is determined by an iterative process. First, one determines final as used concentrations desired of the system. The concentrations are normally stated in terms of molarity. Each biological reagent may have different formulations. Secondly, these concentrations are converted to a weight/dose basis for solids and a volume/dose basis for liquids.

Third, an initial value is chosen for the percent solids concentration of the high viscosity mixture and the desired mixture volume. A 55% solids concentration has been shown to work well. Above a 62% solids concentration the mixture is too stringy for dispensing. If an emulsion is desired, below a 52% solids concentration the mixture is too thin and dries clear and hard. If a semi-emulsion is desired, a lower limit of 10% is permissible. By "% solids" we mean (weight solids×100)÷(weight liquid+weight solids).

The mixture will dry hard and glassy if the glass forming material is allowed to go into solution. Thus, the desired mixture is an emulsion rather than a solution. By emulsion we mean a saturated mixture such that two phases, solid and liquid, are present. For example, the present invention is an emulsion of a glass forming filler material in a biological reagent/buffer solution. The presence of the solids gives the emulsion an opaque to white color.

A high viscosity emulsion still forms a glass when dried, but pores are available on the surface for water to move through and speed dissolution of the dried reagent semi-sphere. The emulsion should have a white color. If it is clear, it most likely will dry hard and glassy, and therefore, will be nonporous. By porosity we mean that the semi-sphere contains pockets of air bubbles which assist in the dissolution of the semi-sphere. A preferred porosity would allow the semi-sphere to dissolve in about 2 minutes or less.

Another version of the invention provides a mixture of glass forming filler material and a biological reagent/buffer solution which we characterize as being a semi-emulsion. By this we mean a mixture having at least some properties of an emulsion. The semi-emulsion of the present invention may be formed by using the above iterative process to arrive at a solids concentration of about 10% to about 50%. The semi-emulsion can then be dispensed onto an inert cyogenic medium to form semi-spheres.

Fourth, one calculates the number of doses that can be made using the grams of glass forming material per dose from the second step.

Fifth, using the number of doses and the weight per dose ratios from the second step, one determines the weights in volumes of the other components. Finally, using the weights and volumes determined in the fifth step, one calculates the percent solids of the final mixture. If the final percent solids of the mixture is out of the 52%–62% range, one repeats the third through sixth steps with another initial value until the final value is in the correct range.

Any potential glass forming material may be evaluated using a protocol according to Example 1, infra, and the iterative process described, supra. Thus, a suitable glass forming material produces a reagent semi-sphere having an acceptable hardness, size, shape, $T_g$, porosity, solubility, and stability (as determined by a functionality test like that in Example 1).

Selection of Glass Forming Filler Material

Examples of glass forming filler materials which may be used in the present invention include carbohydrates such as FICOLL, sucrose, glucose, trehalose, melezitose, DEXTRAN, and mannitol; proteins such BSA, gelatin, and collagen; and polymers such as PEG and polyvinyl pyrrolidone (PVP). The glass forming filler materials are preferably FICOLL polymer, BSA, sucrose, DEXTRAN, or combinations thereof. A most preferred glass forming filler material for use in the present invention is FICOLL polymer.

Selection of a Biological Reagent

Many biological reagents are suitable for storage by the method of the present invention. Also, the biological reagent compositions of the present invention are particularly suitable for performing a wide variety of analytical procedures which are beneficially or necessarily performed on blood plasma or diluted plasma.

The analytical procedures will generally require that the blood plasma be combined with one or more reagent semi-spheres so that some optically detectible change occurs in the plasma which may be related to measurement of a particular component or characteristic of the plasma. Preferably, the plasma will undergo a reaction or other change which results in a changing color, fluorescence, luminescence or the like, which may be measured by conventional spectrophotometers, fluorometers, light detectors, etc. In some cases, immunoassays and other specific binding assays may be performed.

A still further category of biological reagents to which the present invention is applicable is protein and peptides, including derivatives thereof such as glycoproteins. Such proteins and peptides may be any of: enzymes, transport proteins (for example hemoglobin, immunoglobulins, hormones, blood clotting factors and pharmacologically active proteins or peptides).

Another category of biological reagents to which the invention is applicable comprises nucleosides, nucleotides, (such as deoxynucleotides, ribonucleotides and dideoxynucleotides), dinucleotides, oligonucleotides and also enzyme cofactors whether or not these are nucleotides (namely modifying enzymes and restriction enzymes). Enzyme substrates in general are biological reagents to which the invention may be applied.

The biological reagent for stabilization in storage may be isolated from a natural source, animal, plant, fungal or bacterial, or may be produced by and isolated from cells grown by fermentation and artificial culture. Such cells may or may not be genetically transformed cells.

Another development of this invention is to store more than one reagent of a reacting system in a glass reagent semi-sphere. This can be useful for materials which will be required to be used together in, for example, an assay or a diagnostic kit.

Storing the reagents in a single glassy preparation provides them in a convenient form for eventual use. For instance, if an assay requires a combination of a substrate or cofactor in an enzyme, two or all three could be stored in a glassy reagent semi-sphere in the required concentration ratio and be ready for use in the assay.

If multiple reagents are stored, they may be mixed together in an aqueous emulsion and then incorporated together into a glass. Alternatively, they may be incorporated individually into separate glasses which are then mixed together.

When multiple reagents are stored as a single composition (which may be two glasses mixed together) one or more of the reagents may be a protein, peptide, nucleoside, nucleotide, or enzyme cofactor. It is also possible that the reagents may be simpler species. For instance, a standard assay procedure may require pyruvate and NADH to be present together. Both can be stored alone with acceptable stability. However, when brought together in an aqueous solution they begin to react. If put together in required proportions in the glassy reagent semi-sphere, they do not react and the glass can be stored. By react we mean any biochemical reaction.

The preferred biological reagents of the present invention are enzymes and cofactors that provide a reagent system to detect, amplify, modify or sequence nucleic acids. Such enzymes include but are not limited to DNA polymerases (e.g., klenow), T7 DNA polymerase or various thermostable DNA polymerases such as Taq DNA polymerase; AMV or murine reverse transcriptase, T4 DNA ligase, T7, T3, SP6 RNA polymerase, and restriction enzymes. Cofactors include nucleotides, oligonucleotides, DNA, RNA, required salts for enzyme activity (e.g., magnesium, potassium and sodium), and salts required for buffer capacity. Buffer salts provide a proper pH range and aid stability. Some buffers which may be used include Tris pH7.6–8.3.

Any potential biological reagents may be evaluated using a protocol according to Example 1, infra, and the iterative process described, supra. Thus, suitable biological reagents are rendered stable in the reagent semi-sphere as determined by a functionality test like that in Example 1.

Mixing

Various types of mixing were tried using, for example, a standard propeller, disperser, sonicator, roller mill, or shaker. The disperser and sonicator were not successful. Using a standard propeller mixer and adding the powders (reagent and filler) slowly to the liquid was found to work best. Small batches can also be made by stirring the powder into a thin film of liquid on a flat surface. Cooling the mixture while mixing may be required for temperature sensitive biologicals like enzymes. Since an emulsion, and not a solution, is desired, the time between mixing and dispensing should be minimized. The more glass forming filler material allowed to go into solution the harder the mix will dry which will result in a nonporous dried product which is difficult to dissolve.

Dispensing

The final volume per dose of the high viscosity reagent emulsion is often small, such as 2–5 µl, to allow a working volume of 20–50 µl when the semi-sphere is dissolved in a working solution. Dispensing the high viscosity reagent emulsion without causing high shear rates is difficult. However, using a valveless positive displacement pump such as those made by FMI or IVEC has been shown to work well. A time/pressure method such as that used to dispense adhesives also works well. However, using a pinch valve or peristaltic principle produced inconsistent sized drops.

Dispensing Medium

The composition and shape of the drying surface for the dispensed emulsion is important and it determines the drop shape as well as the ease of release from the surface after drying. A TEFLON-coated aluminum pan has worked well, while an uncoated aluminum pan does not. The dried drops stick to the uncoated pan and also spread out in a thin disk. Other coatings on aluminum such as nickel/TEFLON and titanium nitrite also were tried and worked very well. Glass, polystyrene, and wax paper (all unmodified) were unacceptable drying surfaces. However, DELRIN worked very well as a drying surface. One version of a drying surface may contain concave dimples to accept the droplets. Drying continues until the reagent semi-sphere has less than about 10% moisture. By percent moisture we mean (weight water× 100)÷total weight. A preferred moisture is 4%–6%.

A reagent semi-sphere may also be formed by starting with a semi-emulsion as discussed, supra. The semi-emulsion is dispensed onto a cryogenic liquid or onto a cryogenically cooled solid surface. By cryogenic we mean a liquified gas having a normal boiling point below about −75° C., preferably below about −150° C. The preferred cryogenic liquid is nitrogen. The frozen semi-spheres are recovered and then freeze dried to a moisture content of less than about 10%, but preferably about 2%–6%.

Drying Process

1. Emulsions

Vacuum drying, desiccant drying, and freeze-drying of the high viscosity biological reagent droplets were both tried as well as a cycle which combined the techniques. The equipment used was a standard freeze-drier (such as a Virtis GENESIS) with a control modified to allow operation at partial vacuums. Another modification used was to provide a constant purge of dry nitrogen into the chamber to provide gas flow which carried moisture from the product to the condenser.

The problems to overcome in drying were loss of biological activity and loss of droplet shape. If the drying proceeds too quickly, biological activity was lost. Slowing the drying down by increasing the chamber pressure, and lowering the purge gas rate, produced increased biological activity of the dried droplets. Higher pressures also produced more consistently shaped drops. If the pressure was too low, the drops expanded and produced an unacceptable range of shapes. The preferred reagent semi-sphere was produced by keeping the chamber pressure at 300 Torr for the step of drying (about one hour). A typical successful vacuum drying profile is shown below in Table 1.

TABLE 1

| Vacuum (Torr) | Temperature (°C.) | Time (hours) | Nitrogen (SLPM) |
|---|---|---|---|
| 300 | 10 | 1 | 3.5 |
| 90 | 10 | 2 | 3.5 |
| 80 | 10 | 2 | 3.5 |
| 70 | 10 | 2 | 3.5 |
| 60 | 10 | 4 | 3.5 |
| 50 | 20 | 1 | 3.5 |
| 50 | 30 | 1 | 3.5 |
| 50 | 40 | 1 | 3.5 |
| 25 | 50 | 1 | 3.5 |

The temperature of the first five steps can range from 4° C.–20° C., depending on the system.

Other suitable drying profiles may be determined using the techniques in Example 1. Thus, a suitable drying program produces a reagent semi-sphere having an acceptable hardness, size, shape, $T_g$, porosity, solubility, and stability (as determined by a functionality test like that in Example 1).

Freeze-drying and combined freeze/vacuum drying can also be used but require extra time.

A desired percent solids concentration is 52%–62%. The preferred percent solids is about 55%. A typical stability of the reagent semi-spheres is 50%–100% recovered activity. A preferred stability is 80%–100% recovered activity. A desired dissolution rate is 2 minutes or less in 100 μl solution. A preferred dissolution rate is 1 minute or less in 50 μl solution.

2. Semi-emulsions

The semi-spheres formed by dispensing onto a cryogenic surface can be dried by using a freeze-drying process. A typical successful freeze-drying profile is shown in Table 2.

TABLE 2

| Temperature (°C.) | Dwell Time (hours) |
|---|---|
| −46 | 17.0 |
| −36 | 14.0 |
| 0 | 7.0 |
| +28 | 8.0 |

Other suitable drying profiles may be determined using the techniques in Example 7. Thus, a suitable drying program produces a reagent semi-sphere having an acceptable hardness, size, shape, $T_g$, porosity, solubility, and stability (as determined by a functionality test like that in Example 1).

A typical $T_g$ of the reagent semi-spheres (from emulsions and semi-emulsions) is 30° C. A preferred $T_g$ is 45° C. $T_g$ is the glass transition temperature. It is the temperature above which the viscosity of a glassy material drops rapidly and the glassy material turns into a rubber, then into a deformable plastic which at even higher temperatures turns into a fluid.

A typical porosity will allow dissolution of the semi-sphere (from emulsions and semi-emulsions) in 2 minutes or less. A preferred porosity will allow dissolution in 1 minute or less. A typical hardness of the reagent semi-spheres (from emulsions and semi-emulsions) is 4–6 Newtons, but can be as high as 22 Newtons. A preferred hardness is 6 Newtons.

EXAMPLE 1

Preparation of Semi-spheres for T4 ENK Lnd labeling

The formulation and buffer components are determined on a dosage/weight formulation. The final formulation consists of 57.14% solids. A 20X buffer is made using the following protocol.

| Buffer component | 20X concentration | 1X in 50 μl final volume |
|---|---|---|
| Tris pH 7.6 | 1 M | 50 mM |
| $MgCl_2$ | 0.2 M | 10 mM |
| DTT | 0.1 M | 5 mM |
| Spermidine | 2 mM | 0.1 mM |
| EDTA | 2 mM | 0.1 mM |
| ATP | 4 μM | 0.2 μM |
| BSA | 1 mg/ml | 50 μg/ml |

The final formulation is determined utilizing a 20X buffer and the number of reactions to be completed.

| Components | final concentration | 1 reaction | 600 reactions |
|---|---|---|---|
| 20X buffer | 1X | 2.5 μl | 1500 μl |
| T4 PNK | 20 units/rxn | 20 units | 12,000 units |
| FICOLL 40 polymer | 10% final in 50 μl | 4 mg | 2.4 grams |
| water | | 1.051 μl | 630.67 μl |

The wet components consisting of the buffer, enzyme and water are completely mixed. 2.4 grams of FICOLL 400 are weighed into a plastic weigh boat. The liquid mixture is then added to the FICOLL 400 polymer. The components are mixed with a spatula until an emulsion is formed. This will have a consistency of a syrup and the emulsion is typically white. Air bubbles will be present in this emulsion.

The emulsion is poured into a syringe which is attached to the inlet of a pump. A dispensing needle is attached to the outlet of the pump. The emulsion is dispensed by an IVEK model AAA pump to deliver an average predetermined dispensed weight of a wet reaction (in this example, the dispensed weight is 7.27 mg). The dispensing needle attached to the pump is touched to a teflon coated pan for proper dispensing of the emulsion. Samples can be dispensed close to one another, but they should not touch.

The samples are placed in a modified Virtis Genesis freeze dryer with the controls modified to allow operation at partial vacuums. A constant purge of dry nitrogen into the chamber provides gas flow which carries moisture from the product to the condenser. The samples are dried using the parameters shown in Table 1.

Upon completion of the drying process, the samples are stored in a tube that is placed in a foil ziplock bag containing a desiccant pouch.

Stability data includes glass transition, percent moisture, average weight, hardness, solubility and functionality. A Perkin-Elmer DSC7 showed a glass transition temperature of 24° C. Karl Fischer analysis using a Beckmann Coulometer yielded a moisture of 7.2%. The average weight of the semi-spheres is 3.918 mg with a range from 3.581 to 4.442 mg and a standard deviation of 0.332. This sample dissolves in approximately 2 minutes upon addition of 50 µl of water. The hardness testing is carried out in a normal tablet hardness tester (Schleuniger Pharmatron 6D) shows an average hardness of 22 Newtons. Functional analysis involves end labelling of 6 µg (6 pmole ends) of pUC 18/EcoRI/BAP with Gamma $^{32}$P ATP at 37° C. for 30 minutes. A dried sample and a control were purified over a G-50 Sephadex column to remove unincorporated label and counted on a scintillation counter using Chrenkov method. Both control and dried samples showed the same percentage incorporation of radiolabel. The sample was set at room temperature and 37° C. for 3 weeks. The functionality test was completed and the dried samples showed the same percent incorporation as the control sample.

EXAMPLE 2

Preparation of Semi-spheres for PCR

The formulation and buffer component are determined on a dosage/weight formulation. The final formulation is 56.75% solids. A 20X buffer is made utilizing the following protocol.

| Component | 20X concentration | 1X in 100 µl volume |
|---|---|---|
| Tris pH 8.3 | 200 mM | 10 mM |
| KCl | 1 M | 50 mM |
| MgCl2 | 30 mM | 1.5 mM |
| dNTPs | 4 mM each | 0.2 mM |
| BSA | 2 mg/ml | 100 µ/ml |

The formulation is determined utilizing a 20X buffer and the number of reactions to be tested.

| Component | final concentration | 1 reaction | 200 reactions |
|---|---|---|---|
| 20X buffer | 1X | 5 µl | 1 ml |
| AMPLI Taq DNA polymerase | 5 U/rxn | 5 units | 1000 units |
| FICOLL 400 polymer | 10% final in 100 µl | 10 mg | 2 grams |
| water | | 2.73 µl | 547 µl |

The components are mixed, dispensed, dried and stored as in Example 1. Stability data includes glass transition, percent moisture, average weight, hardness, solubility and functionality. A Perkin-Elmer DSC7 shows a glass transition temperature of 58.4° C. The Karl Fischer analysis yielded a moisture of 4.6%. The average weight of these semi-spheres is 9.785 mg with a range of 9.032 to 10.940 mg and a standard deviation of 0.641. This sample dissolved in less than 2 minutes when 100 µl of water is added to the sample. Hardness testing was done with a standard hardness tester shows an average hardness of 5 Newtons.

Functionality was tested after drying and on samples set at room temperature and 37° C. for two weeks. Added to the dried samples were 1 ng of pUC18 and 50 pmoles each of reverse and universal primers and run on a Perkin-Elmer Cetus DNA Thermal Cycler for 95° C. for 1 minute, 58° C. for 1 minute, 72° C. for 1 minute for 40 cycles. All samples run on a 1% agarose gel at 100 volts for 30 minutes stained with ethidium bromide show a band that is the same size and intensity as a control band.

EXAMPLE 3

Preparation of Semi-spheres for Ligation Reactions

The formulation and buffer components are determined on a dosage/weight formulation. The final formulation is 61.8% solids. A 20X buffer is made using the following protocol:

| Buffer components | 20X concentration | 1X in 20 µl final volume |
|---|---|---|
| Tris pH 7.6 | 1.32 M | 66 mM |
| MgCl$_2$ | 0.132 M | 6.6 mM |
| ATP | 2 mM | 0.1 mM |
| Spermidine | 2 mM | 0.1 mM |
| DTT | 0.2 M | 10 mM |

The formulation is determined utilizing a 20X buffer and the number of reactions to be completed.

| Components | final concentration | 1 reaction | 400 reactions |
|---|---|---|---|
| 20X ligase buffer | 1X | 1 µl | 400 µl |
| BSA | 100 µg/ml | 2 µg | 800 µg |
| T4 DNA ligase | 20 units/rxn | 20 units | 8000 units |
| FICOLL 400 polymer | 20% final in 20 µl | 4 mg | 1600 mg |
| water | | 1.78 µl | 711 µl |

The components are mixed, dispensed, dried and stored as in Example 1. Stability data includes glass transition, percent moisture, average weight, hardness, solubility and functionality. A Perkin-Elmer DSC7 showed a glass transition temperature of 73.8° C. The Karl Fischer analysis yielded a moisture of 2.2%. The average weight of these semi-spheres are 4.360 mg with a range of 3.911 to 4.928 mg and a standard deviation of 0.357. This sample dissolved within 5 minutes when 20 pl of water was added. Hardness testing using a standard tablet hardness tester shows an average hardness of 5 Newtons.

Functionality testing was the ligation of 1 µg of λHindIII at 16° C. for 30 minutes. The sample was run on a 1% agarose gel in TBE buffer, stained with ethidium bromide. Samples set at room temperature and 37° C. for 10 days showed 90% ligation of the bands, the same result as the control sample.

EXAMPLE 4

Preparation of Semi-spheres for Nucleotide Stability

This formulation is determined on a 62% dosage/weight formulation. The formulation consists of a mixture of dATP, dGTP, dCTP, dTTP.

| Components | 1 reaction | 500 reactions |
|---|---|---|
| 20 mM each dNTP | 1 µl | 500 µl |
| FICOLL 400 polymer | 5 mg | 2500 mg |
| water | 2 µl | 1 ml |

Mixing, dispensing, drying and storage were completed as in Example 1. Stability data includes glass transition, percent moisture, average weight, hardness, solubility and functionality. A Perkin-Elmer DSC7 showed a glass transition temperature of 86.6° C. The Karl Fischer analysis yielded moisture of 3.6%. The average weight of these semi-spheres are 3.902 mg with a range of 3.430–4.497 mg and a standard deviation of 0.308. These samples dissolved in 2 minutes when 100 μl of water was added to the sample. Hardness testing using a standard tablet hardness tester shows an average hardness of 6 Newtons.

Functionality testing utilizes breakdown of components as analyzed on FPLC. There is a 1.4% breakdown from trinucleotides to dinucleotides after two weeks at room temperature. After two weeks at 37° C., the average breakdown of products is 3.4%.

EXAMPLE 5

Preparation of Semi-spheres for Ribonucleotide Stability

This formulation was determined on a 62% dosage/weight formulation. The formulation consists of ATP, CTP, GTP, UTP.

| Components | 1 reaction | 500 reactions |
| --- | --- | --- |
| 25 mM each rNTP | 1 μl | 500 μl |
| FICOLL 400 polymer | 5 mg | 2500 mg |
| water | 2 μl | 1 ml |

Mixing, dispensing, drying and storage were completed as in Example 1. Stability data includes glass transition, percent moisture, average weight, hardness, solubility and functionality. A Perkin-Elmer DSC7 showed a glass transition temperature of 60.1° C. The Karl Fischer analysis yielded a moisture of 2.2%. The average weight of these semi-spheres is 3.312 mg with a range of 2.959–3.6 mg and a standard deviation of 0.232. These samples dissolved in 2 minutes when 100 μl of water was added. A hardness test using a standard tablet hardness tester shows an average hardness of 6 Newtons.

Functionality testing utilizes breakdown of components as analyzed on FPLC. There is a 1.7% breakdown from trinucleotides to dinucleotides after two weeks at room temperature. After two weeks at 37° C., the average breakdown of products is 2.3%.

EXAMPLE 6

Preparation of Semi-spheres for Restriction Enzymes

Several restriction enzymes have been stabilized by this process including HaeIII, PstI, BamHI, HindIII, BglII, EcoRI. The formulation and buffer components were determined on a dosage/weight formulation. The final formulation is 56.88% solids. A 20X buffer was made using the following protocol.

| Buffer components | 20X concentration | 1X concentration |
| --- | --- | --- |
| Tris pH 8 | 200 mM | 10 mM |
| NaCl | 1 M | 50 mM |
| MgCl₂ | 200 mM | 10 mM |
| DTT | 28 mM | 1.4 mM |
| Tris pH 7.6 | 80 mM | 4 mM |
| KCl | 1.6 M | 80 mM |
| EDTA | 0.8 mM | .04 mM |
| TritonX-100 | 0.8% | .04% |

The formulation is determined utilizing a 20X buffer and the number of reactions to be completed.

| Components | Final concentration | 1 reaction | 1559 reactions |
| --- | --- | --- | --- |
| 20X buffer | 1X | 1 μl | 1559 μl |
| BSA | 100 mg/ml | 2 μg | 3.118 mg |
| FICOLL 400 polymer | 8% final in 20 μl | 1.6 mg | 2.49 g |
| Restriction enzyme | 20 units/rxn. | 20 units | 31,180 units |
| water | | 0.34 μl | 531 μl |

Mixing, dispensing, drying and storage were completed as in Example 1. Stability data includes glass transition, percent moisture, average weight, hardness, solubility and functionality. A Perkin-Elmer DSC7 showed a glass transition temperature ranging from 52° C.–58° C. The Karl Fischer analysis yielded a moisture of 5%–7%. These samples dissolved in approximately two minutes when 20 μl of water was added. A hardness test using a standard tablet hardness tester shows an average hardness of 6 Newtons. One μg of Lambda DNA was digested with the stabilized enzyme buffer mixture at 37° C. for 1 hour. The banding pattern on an agarose gel showed the same banding patterns as the control sample. The dried enzyme/buffer drops were stable after one month at room temperature and 37° C.

EXAMPLE 7

Semi-spheres may be formed by first dripping a semi-emulsion onto a surface of liquid nitrogen and then freeze-drying the resulting frozen semi-spheres. The volume of the semi-spheres can be 5–50 μl but preferably is 10 μl. The solids content of the semi-emulsion on average is 10%–50% by weight. The moisture content of the resulting semi-spheres is less than 10% but preferably 2%–6%. A 20x buffer was made using the following protocol:

| Buffer components | 20X concentration | 1X concentration |
| --- | --- | --- |
| Tris-HCl (pH 7.5) | 200 mM | 10 mM |
| MgCl₂ | 200 mM | 10 mM |
| NaCl | 1000 mM | 50 mM |
| DTT | 200 mM | 10 mM |

The formulation is determined utilizing a 20x buffer and the number of reactions to be completed:

| Component | Final concentration | 1 Reaction | |
| --- | --- | --- | --- |
| 20x Buffer | 2.5X | 2.5 | μl |
| BSA | 125 μl/ml | 0.0125 | mg |
| FICOLL 400 polymer | 12.5% | 1.25 | mg |
| Mannitol | 2.5% | 0.250 | mg |
| Klenow (200 units/ml) | 10 units/reaction | 10 | units |
| 0.8 A₂₆₀ units/ml d(N)₉ | 2 units/reaction | 2 | units |
| dNTP 20 mM | 250 μM | 5 | nmol |

The freeze-drying cycle of Table 2 was utilized.

The final product had the following properties:

Hardness: 4 Newtons

Moisture: 2.8%

$T_g$: 23° C.

Solubility: dissolved in 50 μl of water in 15 seconds

Sample retained 100% of functional activity after two weeks at room temperature.

Although the present invention has been described in considerable detail with reference to certain preferred versions thereof, other versions are possible. Accordingly, the spirit and scope of the appended claims should not be limited to the description of the preferred versions contained herein.

We claim:

1. A method of making a reagent semi-sphere comprising the steps of:
   (a) providing an aqueous solution of a buffered biological reagent;
   (b) mixing a glass forming filler material with the buffered reagent solution to form an emulsion wherein the concentration of the filler material is sufficient to facilitate formation of a glassy, porous composition having a predetermined semi-spherical shape and wherein the emulsion is between 52% and 62% solids;
   (c) dispensing the emulsion in the form of substantially uniform droplets;
   (d) collecting the droplets on an inert medium to form semi-spheres; and
   (e) vacuum drying the droplets, under conditions suitable for maintaining the predetermined semi-spherical shape, to form the reagent semi-sphere;
   wherein the reagent semi-sphere is room temperature stable, water soluble, and has a $T_g$ above room temperature.

2. The method of claim 1 wherein a first portion of the drying is at about 300 Torr and at about 4° C.–20° C.

3. The method of claim 2 wherein the first portion of the drying is about one hour.

4. The method of claim 1 wherein the inert medium is a solid inert surface comprising concave dimples.

5. The method of claim 1 wherein the vacuum drying is continued so that the reagent semi-sphere contains less than about 10% moisture.

6. The method of claim 1 wherein the reagent semi-sphere has a diameter of about 2 mm to about 6 mm.

7. The method of claim 1 wherein at least one reagent semi-sphere is unstable when alone in an aqueous solution at room temperature.

8. The method of claim 1 wherein the aqueous solution contains a plurality of reagents.

9. The method of claim 8 wherein the plurality of reagents react with each other when in aqueous solution.

10. The method of claim 1 wherein the reagent is selected from the group consisting of RNA, DNA, proteins, RNA modifying enzymes, DNA modifying enzymes, restriction enzymes, nucleotides, and oligonucleotides.

11. The method of claim 1 wherein the glass forming filler material is selected from the group consisting of carbohydrates, carbohydrate derivatives which are polyhydroxyl compounds, sugar polymers containing sugar residues linked through either bridges to bifunctional groups other than carbohydrate, mixture of sugars, and proteins.

12. The method of claim 11 wherein the sugar polymer is FICOLL.

13. The method of claim 11 wherein the carbohydrate is sucrose.

14. The method of claim 11 wherein the glass forming filler material is DEXTRAN.

15. The method of claim 11 wherein the protein is selected from the group consisting of gelatin and bovine serum albumin.

16. The method of claim 1 wherein the emulsion is a semi-emulsion containing about 10% to about 50% solids and the inert medium is a cryogenic liquid.

17. The method of claim 1 wherein the emulsion is a semi-emulsion containing about 10% to about 50% solids and the inert medium is a cryogenically cooled solid surface.

18. The method of claim 16 wherein the drying is freeze-drying.

19. The method of claim 17 wherein the drying is freeze-drying.

20. The method of claim 11 wherein the carbohydrates are selected from the group consisting of monosaccharides, disaccharides, trisaccharides, and mixtures thereof.

21. A reagent semi-sphere made according to the method of claim 1.

22. The reagent semi-sphere of claim 21 wherein the carbohydrates are selected from the group consisting of monosaccharides, disaccharides, trisaccharides, and mixtures thereof.

23. A reagent kit comprising:
   at least one reagent semi-sphere according to claim 1;
   a tube containing the at least one reagent semi-sphere; and
   a sealed foil pouch containing the tube and a desiccant.

24. The reagent kit of claim 23 further comprising a dispenser device adapted for individually dispensing the at least one reagent semi-sphere.

* * * * *